US010011867B2

(12) United States Patent
Yu et al.

(10) Patent No.: US 10,011,867 B2
(45) Date of Patent: Jul. 3, 2018

(54) TARGETED SEQUENCING TECHNIQUE FOR WHOLE GENOME DNA METHYLATION

(71) Applicant: FUDAN UNIVERSITY, Shanghai (CN)

(72) Inventors: Wenqiang Yu, Shanghai (CN); Yan Li, Shanghai (CN); Feizhen Wu, Shanghai (CN)

(73) Assignee: Fudan University, Shanghai (CN)

( * ) Notice: Subject to any disclaimer, the term of this patent is extended or adjusted under 35 U.S.C. 154(b) by 339 days.

(21) Appl. No.: 14/902,509

(22) PCT Filed: Nov. 13, 2014

(86) PCT No.: PCT/CN2014/090979
§ 371 (c)(1),
(2) Date: Dec. 31, 2015

(87) PCT Pub. No.: WO2015/070773
PCT Pub. Date: May 21, 2015

(65) Prior Publication Data
US 2016/0376644 A1    Dec. 29, 2016

(30) Foreign Application Priority Data
Nov. 15, 2013 (CN) .......................... 2013 1 0572289

(51) Int. Cl.
*C12P 19/34* (2006.01)
*C12Q 1/6858* (2018.01)
*C12Q 1/6869* (2018.01)

(52) U.S. Cl.
CPC ......... *C12Q 1/6858* (2013.01); *C12Q 1/6869* (2013.01)

(58) Field of Classification Search
None
See application file for complete search history.

(56) References Cited

U.S. PATENT DOCUMENTS 8,440,404 B2 *   5/2013   Makarov ............ C12N 15/1072
                                         435/6.1
9,745,614 B2 *   8/2017   Schroeder ............ C12Q 1/6806
(Continued)

FOREIGN PATENT DOCUMENTS

| CN | 1764729 A | 4/2006 |
|----|-----------|--------|
| CN | 103555856 A | 2/2014 |
| WO | WO-2009/132315 A1 | 10/2009 |

OTHER PUBLICATIONS

International Search Report, PCT/CN2014/090979, Fundan University, 2 pages (dated Feb. 17, 2015).
(Continued)

*Primary Examiner* — Kenneth R Horlick
(74) *Attorney, Agent, or Firm* — Foley & Lardner LLP

(57) ABSTRACT

This invention is directed to a guide positioning sequencing technology of whole-genome DNA methylation. The invention provides a new detection method of nucleic acid methylation. In particular, a concept of "positioning" in the detection of nucleic acid methylation is provided. Specifically, a portion of a sequence is used for genome wide positioning and the other portion of the sequence is used for methylation detection in sequencing, thereby solving/defeating previously existing challenges in methylation detection and bioinformatics analysis of a genome.

14 Claims, 4 Drawing Sheets

(56) References Cited

U.S. PATENT DOCUMENTS

2007/0042365 A1 2/2007 Millar et al.
2009/0269771 A1* 10/2009 Schroeder ............ C12Q 1/6827
　　　　　　　　　　　　　　　　　　　　　　　435/6.12
2010/0120034 A1* 5/2010 McKernan ........... C12Q 1/6827
　　　　　　　　　　　　　　　　　　　　　　　435/6.12

OTHER PUBLICATIONS

Krueger, F. et al., "DNA methylome analysis using short bisulfite sequencing data," Nature Methods, vol. 9, No. 2, pp. 145-151 (Feb. 29, 2012).
English-language machine translation of CN 103555856, Fundan University (Feb. 5, 2014).

* cited by examiner

ACTTAGTCAATTTATCTTGATTTGATATTGCTTACAATTTAGAGATAAATGCA
GATTTCACTTTAACAAGGCATAGTCCCTACATTTTAAAACAAATTTATTTTG
GTGCTTTTCAGGTGGACTTTGTGTTAGCAGTAAGGAAAATAAATAAAAACTA
AACTATTTACCAATAATAACTAAAACATATCCTATATACTACAATACAAATA
AAATATTATAAAAATTTTTTTATTTTTACTTTACTATATTCAAAAAACCATCA
CCTCTTCCCAAAAAAAAAAAATACTTAAAAAAATTAATAAATCTCCACCTAA
AATATTTTCATTAACAAACACAAACTTCACTATTTCAATAAATACAAATACA
AATTTAAAAACAAAACAAAAATTTAAAAACTTAATTTAAACATATCATTAAT
AACTAATAAAAAAACCTATACACTAAATTAAACCTATACTAATTCCTACAAA
TAAAACTATACTAATCATCGACGTTAAATATCTTTTCCAACTAACTACTACA
TCTACCCAATTCACCACTATCCACACCACTCTAAC

Fig. 2

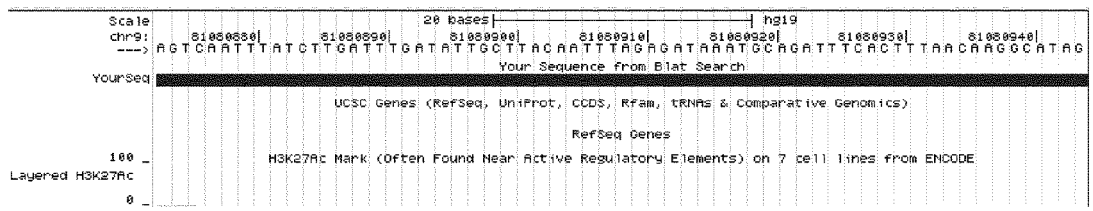

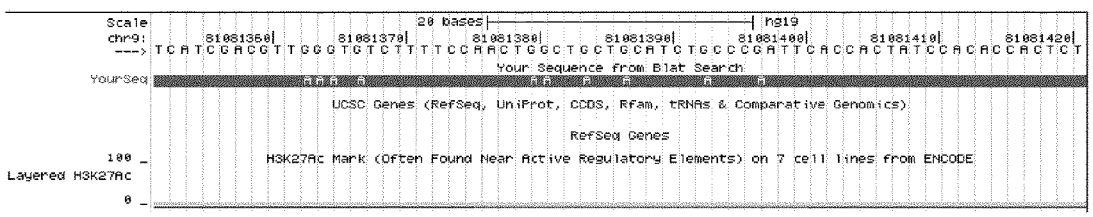

Fig. 3

Human genome DNA sonication

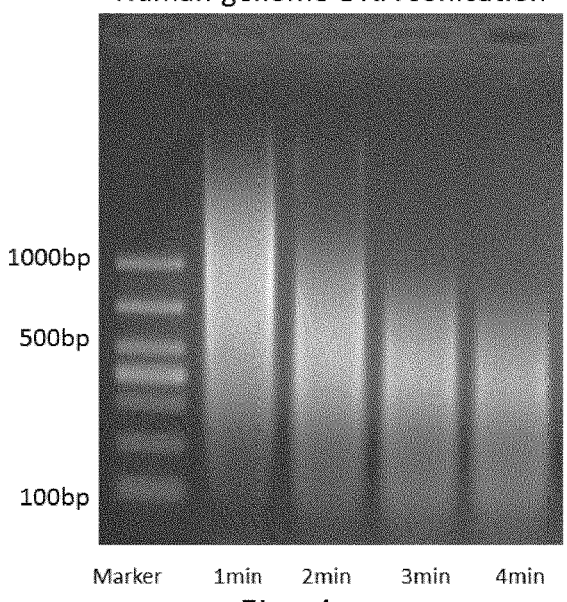

Fig. 4

SEQUENCE LISTING

<160> NUMBER OF SEQ ID NOS: 1

<210> SEQ ID NO 1
<211> LENGTH: 556
<212> TYPE: DNA
<213> ORGANISM: Artificial sequence
<220> FEATURE:
<221> NAME/KEY: misc_feature
<223> OTHER INFORMATION: Polynucleotide

```
<400> SEQUENCE: 1
acttagtcaa tttatcttga tttgatattg cttacaattt agagataaat gcagatttca        60
ctttaacaag gcatagtccc tacatttaaa aacaaattta ttttggtgct tttcaggtgg       120
actttgtgtt agcagtaagg aaaataaata aaaactaaac tatttaccaa taataactaa       180
aacatatcct atatactaca atacaaataa aatattataa aaatttttt attttactt        240 tactatattc aaaaaaccat cacctcttcc caaaaaaaaa aatacttaaa aaaattaata       300
aatctccacc taaaatattt tcattaacaa acacaaactt cactatttca ataaatacaa       360
atacaaattt aaaaacaaaa caaaaattta aaaacttaat ttaaacatat cattaataac       420
taataaaaaa acctatacac taaattaaac ctatactaat tcctacaaat aaaactatac       480
taatcatcga cgttaaatat cttttccaac taactactac atctacccaa ttcaccacta       540
tccacaccac tctaac                                                       556
```

TARGETED SEQUENCING TECHNIQUE FOR WHOLE GENOME DNA METHYLATION

CROSS-REFERENCE TO RELATED APPLICATIONS

The present application is a National Stage of International Application No. PCT/CN2014/090979, filed Nov. 13, 2014, which claims priority to Chinese Application No. 201310572289.X, filed Nov. 15, 2013, which is incorporated herein by reference in its entirety.

TECHNICAL CATEGORY

This invention belongs to the category of molecular biology-epigenetics; more particularly, this invention is directed to a guide positioning sequencing technology for whole-genome DNA methylation detection at single base pair resolution.

BACKGROUND TECHNOLOGY

DNA methylation is an important epigenetic phenomenon that plays a critical role in regulating natural cellular function, embryonic development, disease initiation and tumorgenesis. DNA methylation, especially the levels of methylation across a gene promoter region, directly affects transcription activity and regulates gene expression, thus making DNA methylation a decisive player in cellular biology and behavior. Currently, DNA methylation is considered one the most important research subjects in epigenetics and life science.

A number of methods are known for measuring DNA methylation. They can be classified into the following three categories based on their principles:

1. Methods Based on Methylation-Sensitive Restriction Endonucleases

Methylation-sensitive restriction endonucleases (MSREs) are DNA methylation sensitive endonucleases. The DNA cleavage created by these endonucleases can be blocked as long as there is a methylated base in the restriction site, which is then detected by Southern Blot or PCR. HpaII and MspI are the most commonly used endonuclease pair in methylation detection, wherein both endonucleases recognize the same sequence. However, HpaII is sensitive to methylation while MspI is not. An advantage of such methods is simple manipulation and the disadvantage thereof is the limit of the restriction sites which largely limits the methylation region available to research.

2. Methods Based on the Antibody Against DNA Methylation

This method is based on using an antibody against methyl-cytosine or a DNA methylation-binding protein. The principle and manipulation is similar to ChIP (Chromatin immunoprecipitation). The targeted and purified antibody DNA fragments can be used to hybridize to the microarray (ChIP on chip) or sequenced by next-generation sequencing ChIP-seq. The main advantage of this method is that it allows for studying DNA methylation on a whole genome wide scale. But unfortunately at the same time, it cannot produce accurate methylation measurements at single base resolution. Additionally, the accuracy of the DNA methylation detected by these methods are easily affected by the GC content in the genome DNA sequence, which leads to low accuracy in regions with low GC content.

3. Methods Based on Sodium Bisulfite Conversion

By far, sodium bisulfite conversion is the most widely used method for DNA methylation detection. The advantage thereof allows accurate detection of DNA methylation at single base resolution. The main principle of this method is that un-methylated C (cytosine) can be converted into U (uracil) while methylated C will not change when DNA has been treated by sodium bisulfite. Afterwards, the specific region at which sodium bisulfite has been converted into DNA is amplified via PCR, and the methylation level of this genome region can be obtained by comparing with the original sequence.

DNA methylation has become a hot topic in recent years, and the conventional methods for DNA methylation detection can no longer meet the standards of current research requirements. Owing to the development of high-throughput sequencing. It had been improved and developed from single gene detection to whole-genome level measurement. Many new methods are derived from the combination of the above three methods and high-throughput sequencing technologies, such as MeDIP, RRBS, HELP etc., out of which the most accurate and high genome coverage method is MethylC-seq. The principle of MethylC-seq is to directly sequence the sodium bisulfite converted DNA fragment by next generation sequencing. Theoretically, the methylation level of single base pairs over the whole genome can be obtained through an analysis of sequencing results. However, this analysis process holds numerous obstacles: ① most cytosine (C) in the genome will be converted into thymine (T) after sodium bisulfite treatment and result in an imbalance of nucleotides and low complexity in obtained DNA sequencing reads, which limits its mapping efficiency to reference sequences. Moreover, the methylation information in some low GC content regions cannot be obtained even by increasing the amounts of sequencing output. Therefore so far, we still do not have a complete map of whole genome DNA methylation from any one cell type or tissue. Felix Krueger etc. has described the challenges in analyzing sequencing data of DNA methylation in detail in Nature Method (Nat Methods. 2012 Jan. 30; 9 (2):145-51.); ② there are defects in the design strategy of DNA methylation detection, causing a strong tendency for it to detect only regions with high methylation due to its lack of sensitivity to low methylation, low CG content and repeat sequences.

To sum up, while MethylC-seq is the best method for DNA methylation detection thus far in comparison to other available methods, its design defect, detection tendency thereof and obstacles in bioinformatics analysis greatly hinder its application. In this, we introduce the concept of positioning sequencing, which is used in our invention. It is capable of entirely solving the abovementioned problems and improve whole genome DNA methylation detection overall.

SUMMARY OF THE INVENTION

The objective of this invention is to provide a guide positioning sequencing technology for whole genome DNA methylation detection.

In the first aspect of this invention, a method for determining the status of nucleic acid methylation is provided, wherein said nucleic acid is double-stranded, said method comprises:

(1) Treating the nucleic acid double strands with a polymerase with 3'→5' cleavage function or a 3'→5' exonuclease, so that there is a deletion of 80 to 200 bases, preferably 100 to 150 bases at the 3' end of both strands;

(2) Adding dNTP, wherein cytosine (C) is replaced by methylated cytosine (5mC), so that the deletion at the 3' end of both strands is end-filled and the cytosine thereof is methylated cytosine;

(3) Treating the double strands in step (2) by sodium bisulfate, so that un-methylated cytosine is converted into uracil (U) while methylated cytosine remains unchanged;

(4) PCR amplification (uracil is converted to thymine (T) in this process), DNA methylation status can be determined by next generation sequencing, wherein un-methylated cytosine (C) has been converted into thymine (T) in one portion of a sequence for determining methylation sites; the other portion of the sequence is the same as the original nucleic acid sequence because of the methylated cytosine. The said portion can be then used for sequence positioning in data analysis; comparing the sequence of the two portions (if the sequence of a species is already known, assembly is not needed; for an unknown sequence of a species, the end for positioning sequence is assembled followed by methylation alignment) to obtain the methylation status of the nucleic acid.

In another aspect of the invention, the method for determining nucleic acid methylation can also be used in the detection of a single gene site, wherein step (4) comprises: designing PCR amplification primers for amplifying a gene site of interest, one primer is located in the sequence position where cytosine is methylated; the other primer is located in the sequence position where un-methylated cytosine has been converted into thymine, performing PCR amplification, and lastly obtaining the sequence of the gene site of interest and performing methylation analysis.

In a preferred embodiment, in step (3) or step (b), the double strands are treated with bisulfate, bisulfite, hydrosulfite or bihydrosulfite.

In another preferred embodiment, the nucleic acid is longer than 2 kb (such as longer than 3 kb, 5 kb, 10 kb) or a whole-genome. Prior to step (1), the method further comprises: breaking the nucleic acid (preferably, ultrasonic breaking) to form double-stranded fragments of 200 to 1000 bp (preferably 400 to 700 bp; more preferably 500 bp).

In another preferred embodiment, in step (2), after the end filling, the method further comprises: adding a sequencing adapter to both ends of the double strands in step (2) for high-throughput sequencing.

In another preferred embodiment, the sequencing adapter is linked as follows: adding an protrude A at the 3' end of the double strands, linking them to a sequencing adapter with an protrude T at the 5' end; preferably, the sequencing adapter is a methyl adapter (such as Illumina Methyl Adapter), followed by sequencing with high-throughput sequencing methods, such as Illumina high seq2000, Illumina high seq2500, ABI solid, Roche 454.

In another preferred embodiment, the methylation of cytosine comprises: CpG methylation, CHG methylation or CHH methylation.

In another preferred embodiment, the polymerase with 3'→5' cleavage function includes, but is not limited to: T4 DNA polymerase, T7 DNA polymerase, Klenow enzyme;

The 3'→5' exonuclease includes, but is not limited to: exonuclease III; preferably, when the 3'→5' exonuclease is used in the step (1), the polymerase is also added in the step (2); preferably, the polymerase includes, but is not limited to: Taq enzyme, Pfu, reverse transcriptase.

In another preferred embodiment, the treatment with T4 DNA polymerase lasts for 60 to 140 minutes; preferably 80 to 120 minutes.

In another preferred embodiment, the nucleic acid is DNA or RNA.

In another preferred embodiment, in step (4) or step (c), the same sequence as the original nucleic sequence is one read of the paired-end sequencing, or a portion of a read of single-end sequencing (if single-end sequencing of 100 bp, the former 50 bp is used for positioning and the latter 50 bp is used for methylation detection); preferably, when performing paired-end sequencing, one end in the sequencing results (read1 or read2) of a nucleic acid sequence shows the un-methylated cytosine (C) that has been converted into thymine (T), which can be used for determining the methylation sites; the other end (read1 or read2) of the sequence retains the original nucleic acid sequence because of the methylated cytosine, which can be used for sequence positioning; deductively, when comparing the paired-end sequences, the methylation status of the nucleic acid is thus obtained.

In another aspect of the invention, a method for analysis and alignment of a nucleic acid sequence is provided, the method comprises: the sequencing is paired-end sequencing, one end is used for primary genome position and the other end is used for search nearby said genome position, the method comprises:

(a) positioning one end of a sequence to the genome, allowing positioning each sequence in several positions of genome;

(b) Matching the other end sequence to the reference sequence that has been positioned in genome;

(c) Searching the position of the other end nearby according to the primary genome position in the genome;

(d) Selecting the best alignment position when several alignment positions are available;

(e) Removing the amplified sequences produced by PCR;

(f) Analyzing methylation level of the genome and calculating the percentage of methylation.

In another preferred embodiment, the paired-end sequencing is used for certain lengths that are performed on the 5' and 3' end of a nucleic acid, such as the Pair-End sequencing performed with Illumina Hiseq200, Illumina Hiseq2500, and Illumina Analyzer Genome IIx.

In another preferred embodiment, the positioning of one end of a sequence in genome refers to (but is not limited to) position in 20 positions or less than 50 positions.

In another preferred embodiment, searching nearby for the primary position refers to a search scale of 1 to 3 times the size of the selected sequencing library; the search method includes, but is not limited to: character comparison, regular expression search, sequence search.

In another preferred embodiment, the best alignment position is selected according to: whether the total length between both ends falls into the scope of the library and whether the mismatch number is the lowest.

Other disclosed content is apparent to those skilled in the field according to the disclosure herein.

DESCRIPTION OF FIGURES

FIG. 2 illustrates a representative read of the clone sequencing according to an embodiment of the invention (SEQ ID NO: 1).

FIG. 3 illustrates the alignment result of the clone sequencing result in UCSC genome browser according to an embodiment of the invention.

FIG. 4 illustrates the electrophoresis result of the ultrasonic broken genome in Example 1 according to the invention.

DETAILED DESCRIPTION OF THE INVENTION

Figure 1:
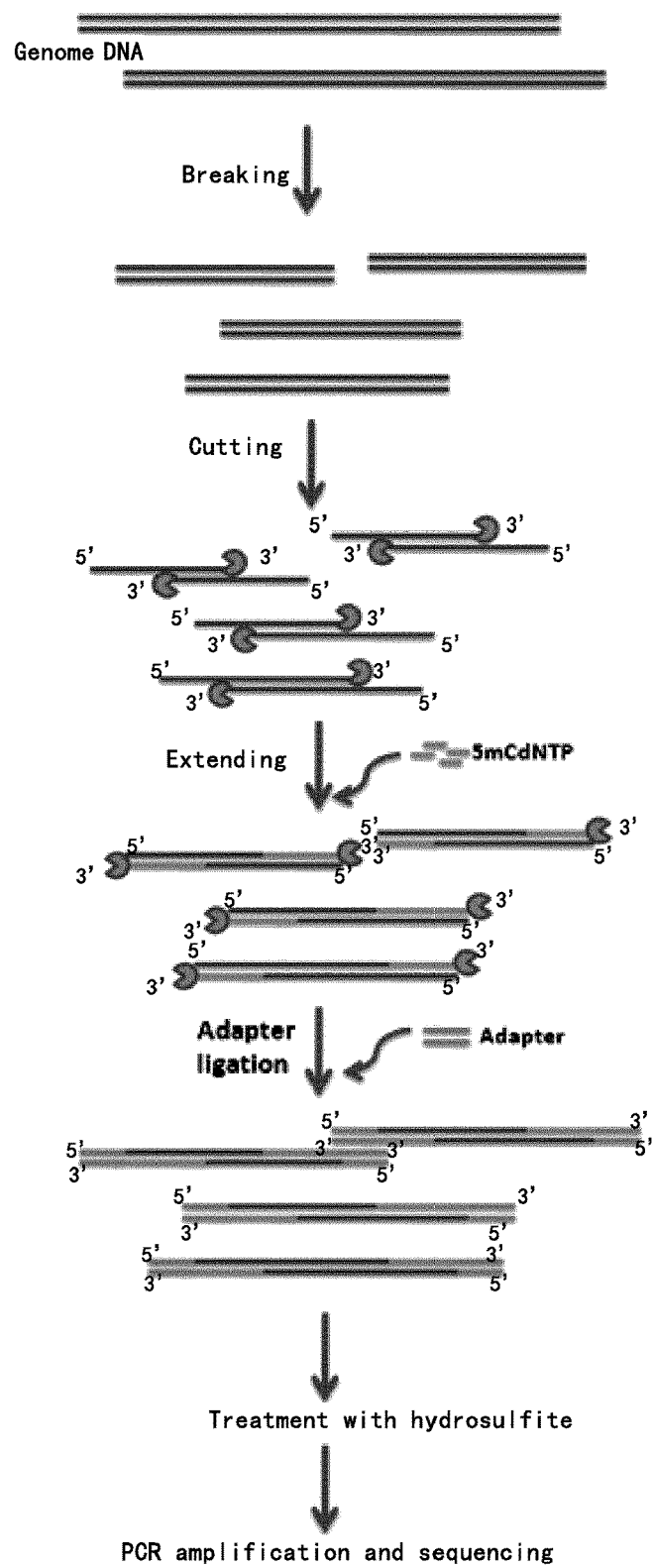
FIG. 1 illustrates the experimental flow-chart according to an embodiment of the invention.

The inventor provides a new methylation detection method of nucleic acid (comprising DNA and RNA). In particular, a "positioning" concept for detection methylation of nucleic acid is provided, which means a portion (as same as the genome sequence) is used for genome positioning and the other portion (un-methylated cytosine is converted into uracil after treatment with sulfite) is used for methylation detection, thereby completely solving the mapping position problems in the bioinformatics analysis for methylation detection. The invention is completed on such basis.

In this invention, nucleic acid double strands are treated with a polymerase with 3'→5' cleavage function or a 3'→5' exonuclease, which generate 3' end deletion in the double strands; then dNTP (wherein cytosine (C) is replaced by methylated cytosine (5mC)) and polymerase is added, which will lead to the extension from 5' to 3' in the deleted region in the double strands to end-fill the deletion at the 3' end of nucleic acid strands and the 5mC is incorporated into the 3' end. Paired-end sequencing is performed after treatment with sodium bisulfite or the analogs thereof, C will be converted into T in one end of sequencing (read1), and the original genome sequence remains unchanged in the other end (read2) due to the cytosines being all methylated, so that the methylation of genome can be analyzed with read1 and the mapping position in the genome can be done with read2, which completely solves the problems in data analysis of methylation detection.

The enzyme that generates 3' deletion can be a polymerase with 3'→5' cleavage function or a 3'→5' exonuclease. Wherein the polymerase with 3'→5' cleavage function includes, but is not limited to: T4 DNA polymerase, T7 DNA polymerase, Klenow enzyme. The 3'→5' exonuclease includes, but is not limited to: exonuclease III.

As a preferred embodiment according to the invention, a polymerase with 3'→5' cleavage function is used; when 3' end deletion needs to be produced in the double strands, said polymerase can work with its 3'→5' cleavage function; when 3' end needs to be extended after adding dNTP, said polymerase can work with its polymerase function. Most preferably, the polymerase with 3'→5' cleavage function is T4 DNA polymerase.

When a 3'→5' exonuclease is used to generate deletion at 3' end, a polymerase should be added to extend the 3' end when dNTP is present.

Bisulfite sequencing PCR (BSP) method is a classic method for methylation detection of a gene, the principle thereof is: treating the genome DNA with sodium bisulfite, all the un-methylated cytosines (C) are converted into uracils (U) and methylated cytosines remain unchanged. Therefore, after treatment with sodium bisulfite or bihydrosulfite, the methylated site generates a C/T like single nucleotide polymorphisms (SNP). After the genome DNA is treated with sodium bisulfite, the target fragment is amplified, then uracils (U) are all converted into thymines (T), and finally the methylation status is determined by sequencing of the PCR product.

The method according to the invention is suitable for longer nucleic acids, such those longer than 10 kb or whole-genome. Yet at the same time, it can also be used in short nucleic acids. As for nucleic acids with distinct lengths, it is necessary to control the length when the nucleic acids are broken. For example, the ultrasonic breaking time can be used to control the length. For longer nucleic acids, the nucleic acid sequence is needed to be broken to benefit the following manipulation. The invention does not limit the method for breaking nucleic acids, various known methods can be used; preferably, ultrasonic breaking can be used. The ultrasonic condition mainly depends on the ultrasonic equipment, the G+C content of a nucleic acid and the size of desired fragment, etc. For ultrasonic breaking with the non-contact ultrasonic instrument from BioRuptor, if the G+C content of genome is about 50%, ultrasonic breaking is performed at maximum power for 6 times, each time with 30 second for sonication and 30 second pauses from sonication to obtain fragments of about 400 to 700 bp. With distinct ultrasonic systems, if a better condition is necessary, the size of broken sequence fragments can be obtained according to electrophoresis results.

As a preferred embodiment according to the invention, a long nucleic acid or genome is broken to generate double strands fragments of 200 to 1000 bp; preferably 400 to 700 bp; more preferably 500 bp.

When the methylation detection is performed on a long nucleic acid sequence or a whole-genome, a high-throughput sequencing technology is needed. At this time, when the deletion at the 3' end of the double strands is end-filled and the cytosines thereof are methylated cytosines, the technology further comprises: adding a sequencing adapter to both ends of the end-filled double strands for high-throughput sequencing. In this invention, a sequencing adapter refers to a nucleic acid adapter involved in some high-throughput sequencing technologies, those who are skilled in the relative field clearly know the sequencing adapter used in any particular sequencing technology. For example, the sequencing technology from Illumina has provided powerful high-throughput sequencing methods for users, which provides a commercial sequencing adapter for linkage between sequences to be sequenced and sequencing instrument; other sequencing technologies and the sequencing adapters thereof other than the Illumina sequencing technology are also commercial or known to those skilled people in the relative field.

The method according to the invention is also suitable for sequencing a single nucleic acid strand, by incorporating dNTP wherein cytosine (C) is methylated when the second strand is synthesized, the bases remain unchanged in one strand of the synthesized nucleic acid double strands and the un-methylated cytosine is converted after the following treatment with hydrosulfite. Therefore, one strand is used for positioning and the other strand is used for methylation detection in sequencing.

More over, the method according to the invention can be used not only in directly detecting methylation levels of the whole genome, but also to combine with other methods, such as RRBS to increase the map efficiency in RRBS. Furthermore, the method can also sequence for unknown species by assembly sequences with read2 and detect methylation level with read1, thereby obtaining the genome sequence of the species and the methylation level thereof. The methylation sequencing according to the invention refers to the methylation of cytosine comprising CpG methylation, CHG methylation and CHH methylation.

The invention has overcome the defects in existing methylation detection technologies for high-throughput and high resolution, the study of the distribution of DNA methylation at single base revolution in whole genome can be achieved, and, the information of epigenome and genome can both be obtained.

With reference to specific embodiments, the present invention is further illustrated. It should be understood that these embodiments are merely illustrative of the invention and are not intended to limit the scope of the invention. The specific condition for the experimental methods not illustrated in the following examples is generally in accordance with conventional conditions, such as the conditions described in Sambrook, J., eds, Molecular Cloning, A Laboratory Manual, Academic Press, 2002, or the conditions recommended by the manufacturer.

The following examples mainly detect the genome DNA methylation in tissues and cells, wherein the whole process comprises: ultrasonic breaking DNA, treatment with a T4 DNA polymerase, adding "A" at the ends, linking adapters, removing the adapters by gel purification, treatment with sodium bisulfite, PCR amplification, etc., and the main process is shown in FIG. 1.

Example 1. Ultrasonic Breaking DNA

3 μg of the extracted genome DNA from human cell line 293T is dissolved in 250 μl of pure water, the DNA is broken into fragments of about 400 to 700 bp with suitable ultrasonic conditions, the ultrasonic product is recovered with PCR purification kit from QIAGEN, wherein the special manipulation step is as follows: adding 5× volume (1 ml) of PB buffer to the ultrasonic product, flicking to completely mix, short-spin, transferring to a column, 13000 rpm for 1 min. The elution liquid is removed. 750 μl of buffer PE (added with ethanol) is added, 13000 rpm for 1 min, and the liquid is removed as above. Again, 500 μl of buffer PE is added, and the column is washed again, the liquid is removed, the lid is uncovered and the column is idled standing for 2 min, lid is opened and the column stands for drying. 170 μl of ultrapure water is added and the column stands for 1 to 2 min, 13000 rpm for 1 min, with the elution liquid collected and reserved.

The electrophoresis of ultrasonic broken genome is performed and the result is shown in FIG. 4, wherein DNA has a length of 1000 bp to 200 bp after 3 min ultrasonic and the length mainly distributed around 500 bp.

Example 2. Treatment with T4 DNA Polymerase

The following agents are added successively to the recovered product:

| 10× NEB buffer 2 | 2 μl |
| T4 DNA polymerase | 10 μl |

The product is flicked to completely mix, short-spin (1000 g for 30 s) and digested at 12° C. for 100 min to cut off about 100 to 150 bases at the 3' end; thereafter, dNTP with a final concentration of 10 mM (wherein cytosine is methylated cytosine, that is 5mC) is added, the product is flicked to completely mix, short-spin (1000 g for 30 s), and at 37° C. for 15 min. PCR purification (the process as above) is performed, finally elute the column with 42 μl of ultrapure water for collection and reserve.

Example 3. Adding One "A" at 3' End

The following agents are added successively to the recovered product:

| 10× NEB buffer 2 | 5 μl |
| 10 mM dATP | 1.5 μl |
| Klenow without the activity of 3'→5' exonuclease | 3 μl |

The product is flicked to completely mix, short-spin, at 37° C. for 1 h, recovered with Mini Elute PCR purification kit from QIAGEN, and eluted with 17.5 μl of ultrapure water for collection and reserve.

Example 4. Adapter Linkage

The following agents are added successively to the recovered product:

| 10× T4 DNA linkage buffer | 2.5 μl |
| Illumina methyl adapter (Illumina Methyl Adapter) | 5 μl |
| T4 DNA ligase | 1 μl |

The product is flicked to completely mix, short-spin and linked at 16° C. overnight. Wherein, Illumina Methyl Adapter is an adapter produced by illumina for methylation high-throughput sequencing.

Example 5. Removing the Redundant Adapters by Gel Purification

1. Gel Preparation

2% (by weight) of agarose (Invitrogen) is formulated with 80 to 90 ml of TAE, boiled for 2 to 3 times in the microwave oven and 3 μl of EB is added when the bottle is not so hot, the formulation is mixed completely and poured on plates.

2. Electrophoresis

5 μl 10×loading buffer is added to the sample, 100 bp marker is prepared and the marker is added in two sides while the samples are added in the middle, it is noted that a hole is kept between different samples to prevent contamination. Electrophoresis is performed at 150V for 40 minutes.

3. Cutting Gel

The UV Gel Imaging stage is washed by paper dipped with TAE and then a preservative film is spread on the stage. The radiation time of gel under UV is minimized. The 15 ml centrifuge tube is weighed and recorded. The gel fragment of 400 to 700 bp is cut and the photos of the gel before/after cutting are recorded, the gel is put into a tube. The tube with gel is weighed and recorded.

4. Gel Recovery

The DNA in the gel is recovered with Gel Extraction mini elute kit from QIAGEN, 100 mg=100 μl volume, 3× volume of Buffer QG is added, at 42° C. for 10 min, mixing is performed every 2 to 3 minutes until complete dissolution. After short-spin, 1× volume of isopropanol is added, short-spin, each time 750 μl buffer PE is loaded in Elute column, 13000 rpm for 1 minute, 500 μl of Buffer QG is added followed by centrifugal for 1 min. 750 μl of Buffer PE is added followed by centrifugal for 1 minute, 500 μl of buffer PE is added again for wash followed by standing idly for 2 min, the lid is opened and stand for drying, 22 μl of ultrapure water is added and stand for 1 to 2 min, 13000 rpm for 1 min, the product is recovered for reserve.

Figure 5:
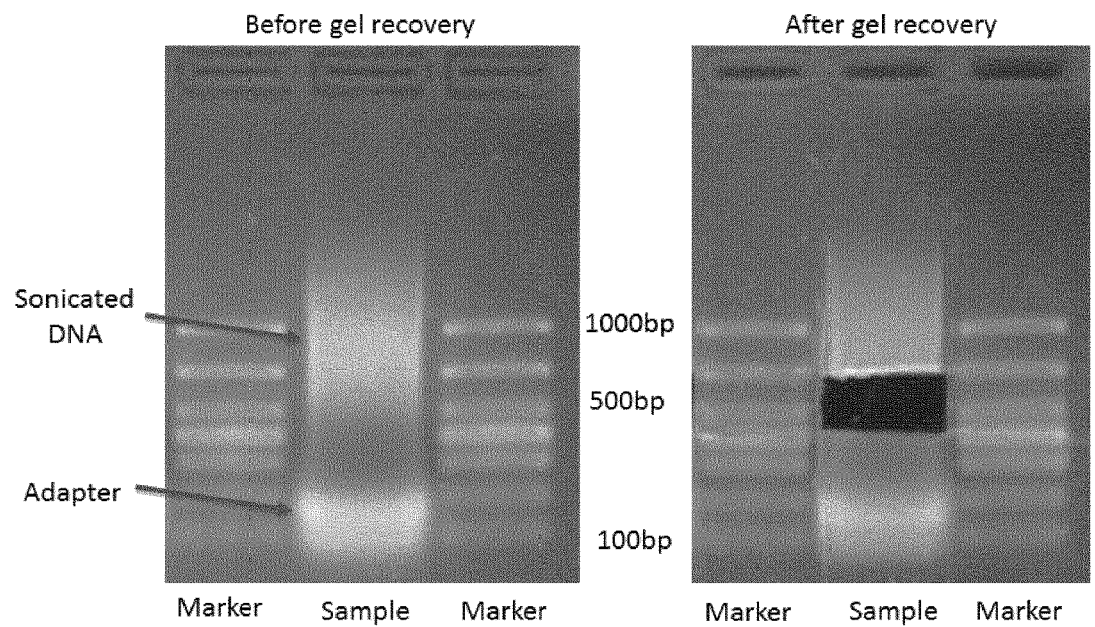
FIG. 5 illustrates the result of removing redundant adapters by gel purification in Example 5 according to the invention.

The result of removing a redundant adapter by gel recovery is shown in FIG. 5, the large fragment above 400 bp in the left panel is the genome DNA after ultrasonic treatment and the small fragment of about 200 bp is the adapter DNA to be removed. The right panel shows the gel photo after cutting, wherein the DNA of 400 to 700 bp has been cut off and recovered.

Example 6. Treating DNA with Sodium Bisulfite

The above recovered product is treated with a DNA methylation kit from Zymo-Research, 20 μl of recovered product is added to 130 μl of CT Conversion Reagent, the samples after short-spin is loaded in a PCR instrument with a reaction program set as follows: 98° C., 10 min; 64° C., 2.5 h; 4° C., ∞; the Zymo column (Zymo-Spin™ IC Column) is placed into Collection Tube, 600 μl of M-Binding Buffer is added, then the samples after reaction are added, the lid is closed tightly followed by upside down mixing; 12,000 rpm (<10,000 g) for 30 s; 100 ul of M-Wash Buffer is added, 12,000 rpm for 30 s; 200 ul of M-Desulphonation Buffer is added, at room temperature (20~30° C.) for 15 to 20 minutes, 12,000 rpm for 30 s; 200 μl of M-Wash Buffer is added, 12,000 rpm for 30 s, the waste liquid is removed in the collection column; wash once more; the column is transferred into a clean 1.5 ml EP tube, 10 μl of M-Elution Buffer is added at the bottom of the column, 12,000 rpm for 30 s, with the eluent collected and reserved.

Example 7. PCR Amplification

Because the C is converted into U in DNA after the treatment with sodium bisulfate, the widely used high-fidelity enzymes cannot recognize U and thus fail to amplify the treated fragments. 2×KAPA mix from KAPA is used in the experiment, thus overcoming such problems.

The following agents are added to a PCR tube:

| | |
|---|---|
| 2× KAPA mix | 25 μl |
| DNA | 10 μl |
| Primer F | 1 μl |
| Primer R | 1 μl |
| H₂O | up to 50 μl |

Reaction Condition

| | | |
|---|---|---|
| 98° C. | 30 s | |
| 98° C. | 10 s | |
| 65° C. | 45 s | } 12 cycles |
| 72° C. | 45 s | |
| 72° C. | 3 min | |

Figure 6:
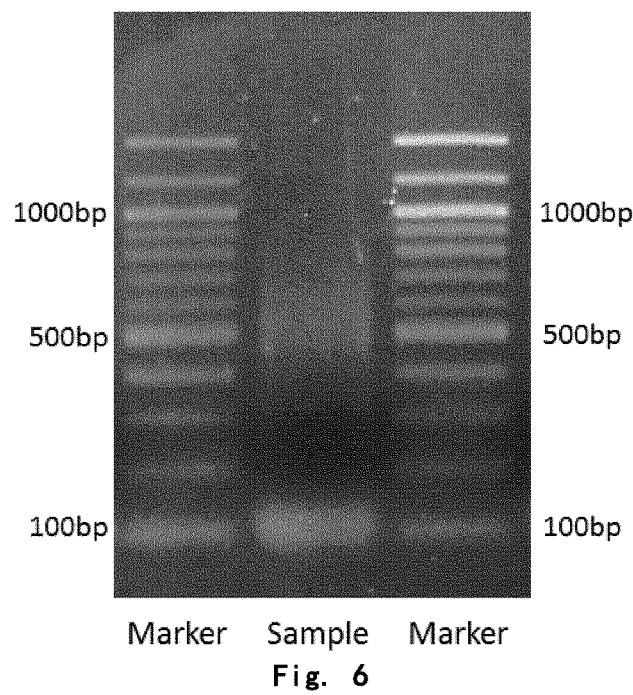
FIG. 6 illustrates the electrophoresis result after PCR in Example 7 according to the invention, wherein the illustrated DNA fragment is 400 to 700 bp.

The electrophoresis of the PCR product is performed and the result is shown in FIG. 6, wherein the DNA fragment has a length of 400 to 700 bps that is consistent with the size of the gel recovery in Example 5.

After electrophoresis, the gel is recovered and the high-throughput sequencing can be performed after quantification.

FIG. 2 illustrates a read of genome DNA high-throughput sequencing. Wherein the shadow region is incorporated with methylated C, which means the region is used for positioning in data analysis. It can be seen from the result that C and G bases are both present at the 5' end in the shadow region (corresponding to the end for positioning in high-throughput sequencing) of the sequencing result, and there is only C and no G at the 3' end (corresponding to the end for methylation detection in high-throughput sequencing) of the sequencing result (the original result should be that there is only G and no C, for the anti-sense strand is clone-sequenced), which means the method has met the requirement of high-throughput sequencing.

FIG. 3 shows the alignment result of the clone sequencing result according to an embodiment of the invention in UCSC genome browser, the upper part of the figure shows that the sequencing result is same as the original genome (the portion for positioning) and the lower part of the figure shows that all G other than CG has been converted into A (the portion for methylation detection).

Figure 7:
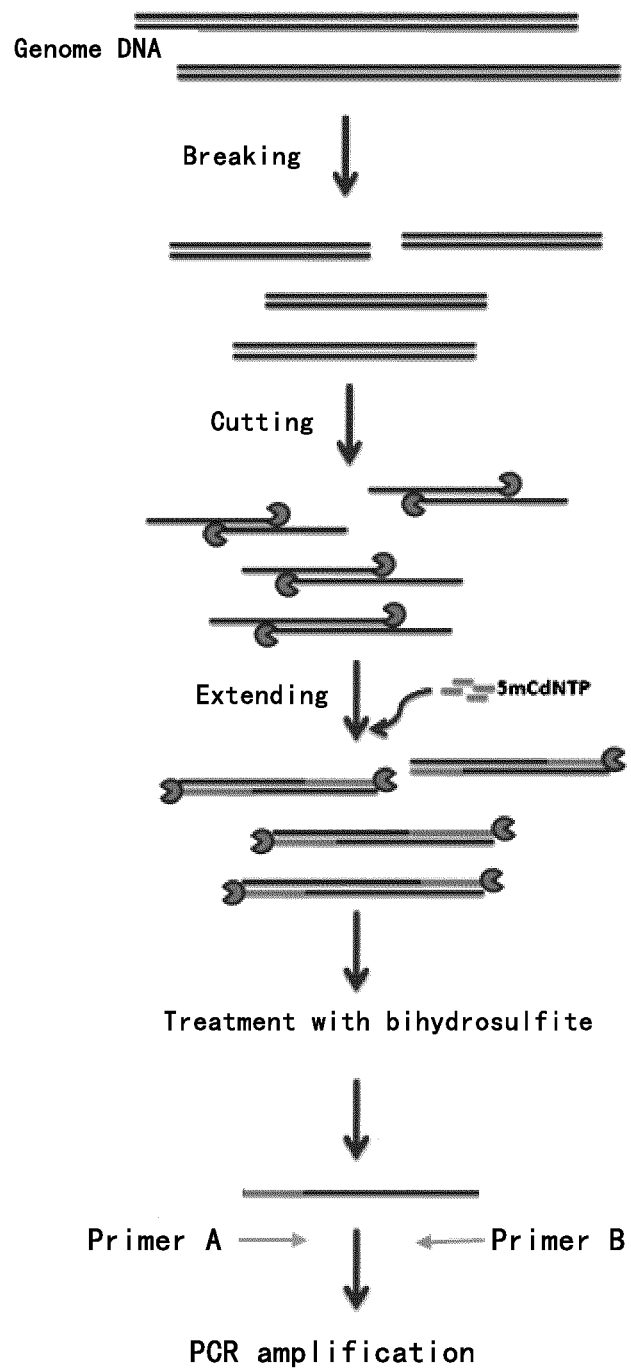
FIG. 7 illustrates the experimental flow-chart of detection of a single gene site.

The method according to the invention can also be used in the detection of a single gene site and the experimental flow-chart thereof is illustrated in FIG. 7. By designing the PCR amplification primers for amplifying a gene site of interest, one primer is localized in the sequence position where the cytosine is methylated; the other primer is localized in the sequence position where un-methylated cytosine has been converted into thymine, after PCR amplification, the sequence of the gene site of interest is obtained and methylation analysis is performed.

All the documents mentioned in the present application are cited by reference, as if each document was individually incorporated by reference. It should also be understood that after reading the content of the teaching, those skilled in the field can make various modifications or improvements to the present invention, these equivalent forms also fall within the present application as defined by the appended claims scope.

The invention claimed is:

1. A method for detection of nucleic acid methylation status, wherein said nucleic acid is double-stranded, said method comprises:
   (1) treating the nucleic acid double strands with a polymerase with 3'→5' cleavage function or a 3'→5' exonuclease, so that there is a deletion of 80 to 200 bases at the 3' end of both strands;
   (2) adding dNTP, wherein cytosine (C) is methylated cytosine (5mC), so that the deletion at the 3' end of both strands is end-filled and cytosine thereof is methylated cytosine;
   (3) treating the double strands in step (2), so that unmethylated cytosine is converted into uracil (U) while the methylated cytosine remains unchanged;
   (4) PCR amplifying and sequencing the nucleic acid to determine the methylation status of the nucleic acid, wherein the un-methylated cytosine has been converted into thymine in a portion of a sequence for determining a methylation site; the other portion of the sequence is the same as the original nucleic acid sequence because the cytosine has been methylated.

2. The method according to claim 1, wherein in step (3), treating the double strands in step (2) comprises treatment with bisulfate, bisulfite, hydrosulfite or bihydrosulfite.

3. The method according to claim 1, wherein the nucleic acid is a nucleic acid longer than 2 kb or comprises a whole-genome, and prior to step (1), the method further comprises: breaking the nucleic acid sequence to generate double-stranded fragments of 200 to 1000 bp.

4. The method according to claim 1, wherein the method is used for detection in a gene site of interest, wherein step (4) comprises:
   designing PCR amplification primers for amplifying the gene site of interest, in which one primer is located in a sequence position where cytosine is methylated; the other primer is located in a sequence position where un-methylated cytosine have been converted into thymine, performing PCR amplification, obtaining the sequence of the gene site of interest and performing methylation analysis.

5. The method according to claim 1, wherein in step (2), after end-filling, the method further comprises: adding a sequence adapter at both ends of the double strands in step (2) for high-throughput sequencing.

6. The method according to claim 5, wherein the adapter is linked as follows: adding a protruding A at the 3' end of the double strands, and linking the double strands to a sequencing adapter with a protruding T at the 5' end.

7. The method according to claim 6, wherein the sequencing adapter is a methyl adapter, and wherein the sequencing of step (4) comprises high-throughput sequencing methods.

8. The method according to claim 1, wherein the methylation of cytosine comprises one or more selected from the group consisting of: CpG methylation, CHG methylation and CHH methylation.

9. The method according to claim 1, wherein the polymerase with 3'→5' cleavage function comprises one or more enzymes selected from the group consisting of: T4 DNA polymerase, T7 DNA polymerase, and Klenow enzyme; and wherein the 3'→5' exonuclease comprises exonuclease III.

10. The method according to claim 9, wherein when the 3'→5' exonuclease is used in step (1), the polymerase is also added in step (2).

11. The method according to claim 10, wherein the polymerase comprises one or more enzymes selected from the group consisting of: Taq enzyme, Pfu, and reverse transcriptase.

12. The method according to claim 1, wherein in step (4), the same sequence as the original nucleic sequence is one read of paired-end sequencing, or a portion of a read of single-end sequencing.

13. The method according to claim 12, wherein the paired-end sequencing is performed, wherein one end of a nucleic acid sequence in which the un-methylated cytosine has been converted into thymine is used for determining the methylation sites and the other end of the sequence, which retains the original nucleic acid sequence because of the methylated cytosine is used for sequence positioning.

14. The method according to claim 1, wherein in step (4), the sequencing method of a nucleic acid is paired-end sequencing, wherein one end is used for primary positioning and the other end is used for searching, the method comprises:
   (a) localizing one end of a sequence to the genome, allowing the positioning of each sequence in several positions within the genome;
   (b) matching the other end sequence to the sequence that has been positioned in genome;

(c) searching the position of the other end nearby according to the primary positioning in genome;
(d) selecting the best alignment position when several alignment positions are available;
(e) removing an amplified redundant sequence produced by PCR;
(f) analyzing methylation level of the genome and calculating the percentage of methylation.

* * * * *